United States Patent [19]
Drevet et al.

[11] Patent Number: 5,643,195
[45] Date of Patent: Jul. 1, 1997

[54] DEVICE FOR REGULATING THE FLOW OF CEREBROSPINAL FLUID IN A DRAINAGE CIRCUIT

[76] Inventors: Jean-Baptiste Drevet, 45 boulevard Saint-Michel 75005, Paris; Serge Glories, Le Laurier Palaja 11570, Cazilhac, both of France

[21] Appl. No.: 424,490

[22] PCT Filed: Nov. 30, 1993

[86] PCT No.: PCT/FR93/01176

§ 371 Date: May 17, 1995

§ 102(e) Date: May 17, 1995

[87] PCT Pub. No.: WO94/12222

PCT Pub. Date: Jun. 9, 1994

[30] Foreign Application Priority Data

Nov. 30, 1992 [FR] France ................................. 92 14413

[51] Int. Cl.⁶ ............................................................ A61M 5/00
[52] U.S. Cl. ............................................. 604/9; 604/247
[58] Field of Search .............................. 604/7, 8, 9, 10, 604/247

[56] References Cited

U.S. PATENT DOCUMENTS

| | | |
|---|---|---|
| 3,886,948 | 6/1975 | Hakim . |
| 4,127,110 | 11/1978 | Bullara . |
| 4,464,168 | 8/1984 | Redmond et al. ............... 604/9 |
| 4,551,128 | 11/1985 | Hakim et al. . |
| 4,557,721 | 12/1985 | Hooven ............................ 604/9 |
| 4,627,832 | 12/1986 | Hooven et al. ................... 604/9 |
| 4,657,530 | 4/1987 | Buchwald et al. . |
| 4,705,499 | 11/1987 | Hooven ............................ 604/9 |
| 4,781,672 | 11/1988 | Hooven ............................ 604/9 |
| 4,867,741 | 9/1989 | Portnoy . |
| 5,304,114 | 4/1994 | Cosman et al. .................. 604/8 |

FOREIGN PATENT DOCUMENTS

| | | |
|---|---|---|
| 0233325 | 8/1987 | European Pat. Off. . |
| 2372366 | 6/1978 | France . |

*Primary Examiner*—John G. Weiss
*Assistant Examiner*—Ki Yong O
*Attorney, Agent, or Firm*—Sixbey, Friedman, Leedom & Ferguson, P.C.; Gerald J. Ferguson, Jr.; Tim L. Brackett, Jr.

[57] ABSTRACT

A device for regulating the flow of an organic liquid between a production site and a resorption site of a patient in a drainage circuit that extends between the two sites, one of the sites being a site of small pressure variation and the other being a site of large pressure variation, particularly as a function of the position of the subject, the device comprising a valve for implanting beneath the skin and connected by a first duct to one of the sites and by a second cut to the other site, the valve comprising a body (1) defining an internal passage inter-connecting the two ducts, a member (14) for adjusting the section of said passage, and control means (7, 15) coupled to said adjustment member (14) to displace it between a first position in which the passage is closed and second positions in which the passage is opened to a controlled extent, the device being characterized in that the control means comprise a first chamber (12) formed in the body (1) and closed in sealed manner by a moving wall (7), a second chamber (6) formed in the body and separated from the first by the moving wall (7), which second chamber forms a portion (2) of the interconnecting passage and is connected to the duct (3) coming from the site having small pressure variation, means for coupling the moving wall (7) to the adjustment member (14), resilient means (17, 21) for returning the adjustment member towards its position in which it closes the interconnecting passage, and means for adjusting the magnitude of the return force.

16 Claims, 4 Drawing Sheets

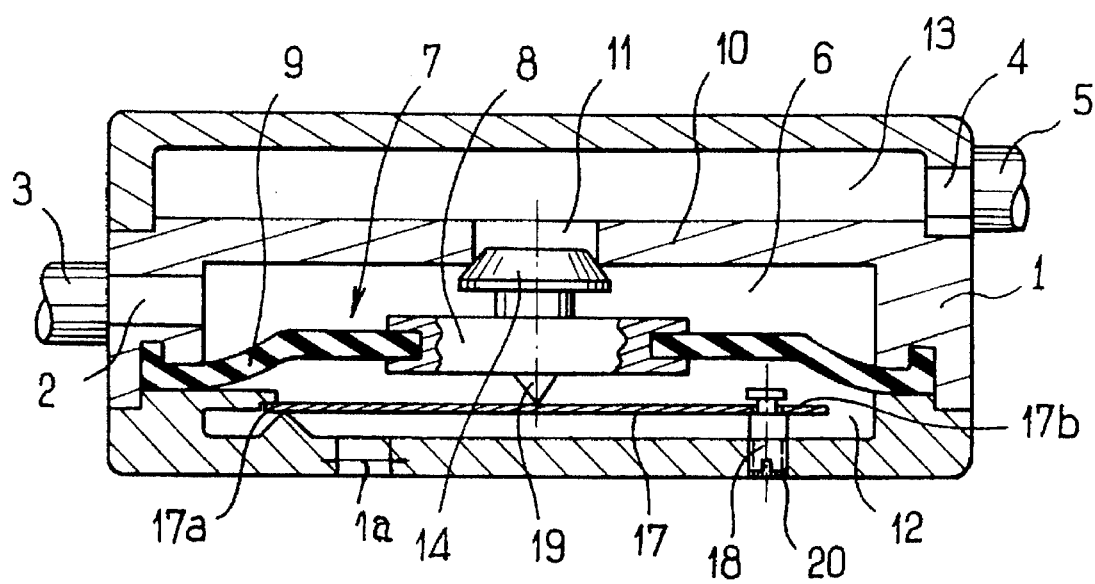
FIG_1
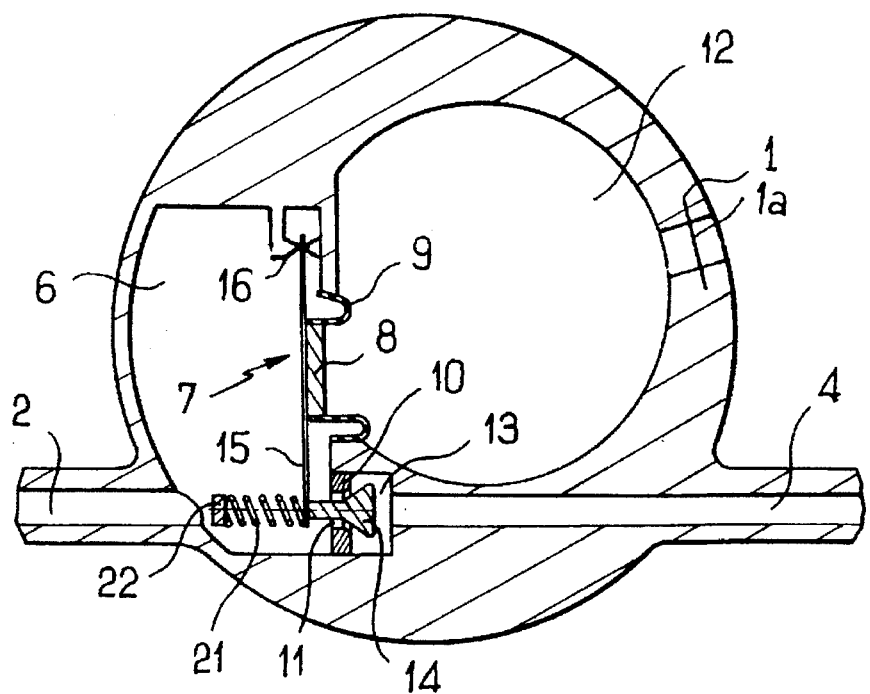
FIG_2

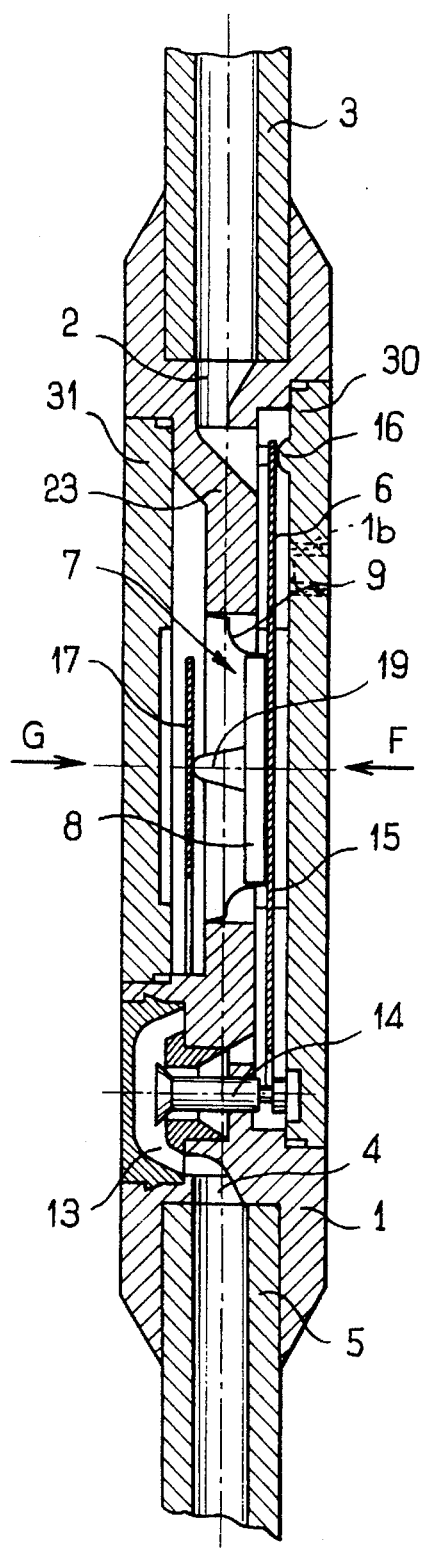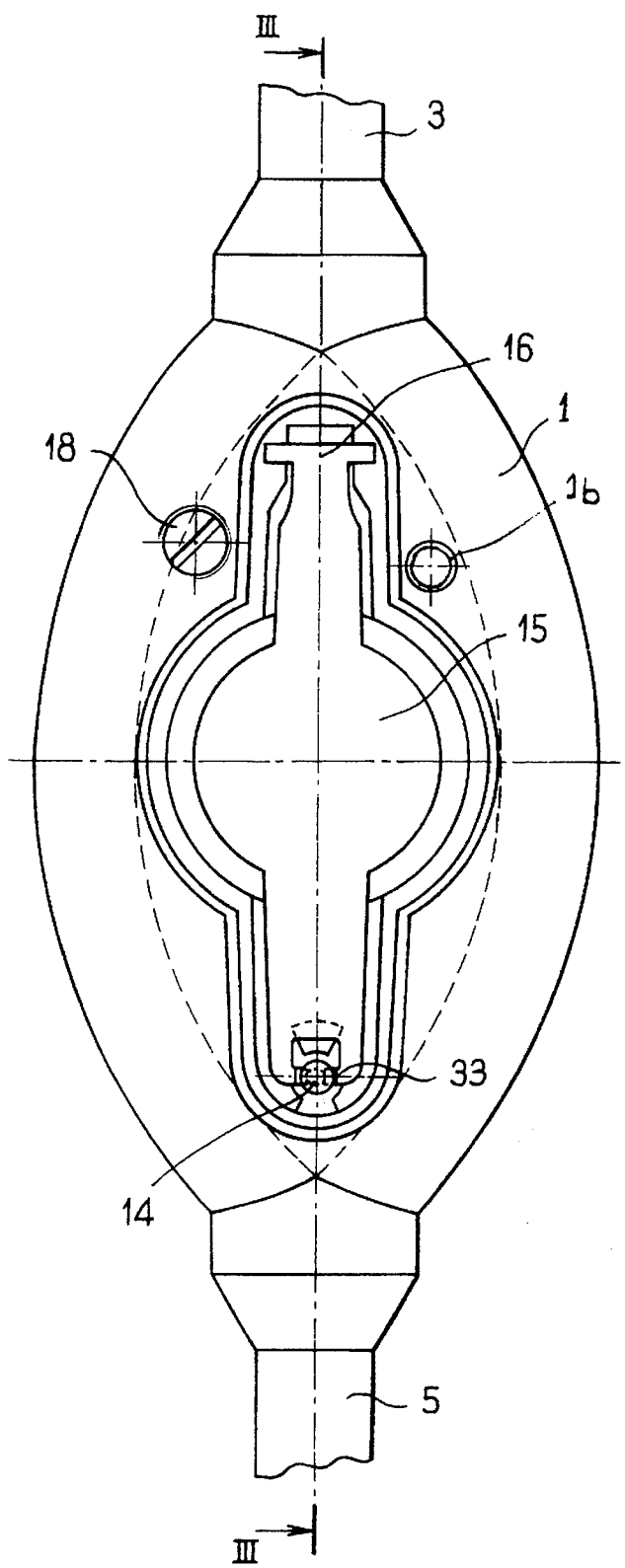
FIG_3  FIG_4

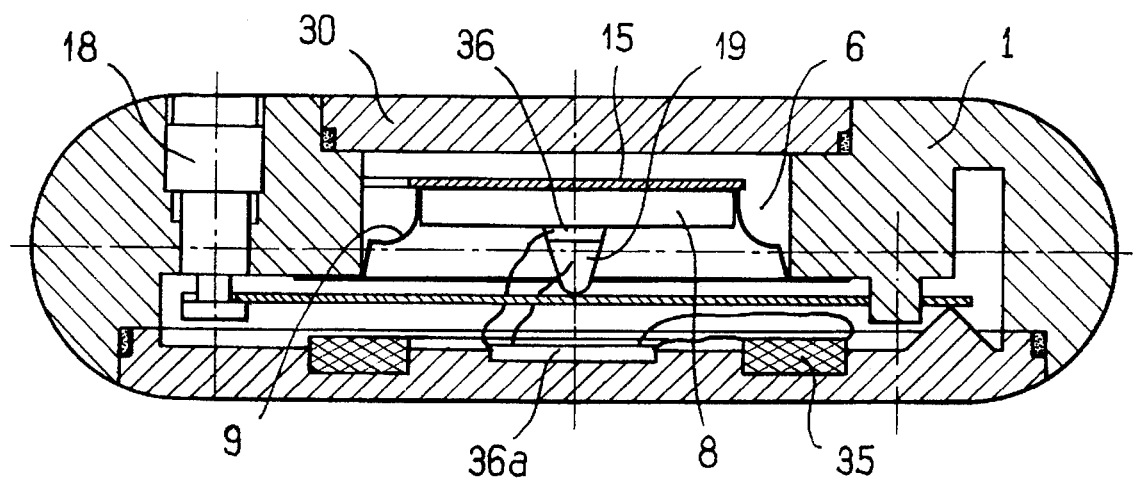
FIG_7
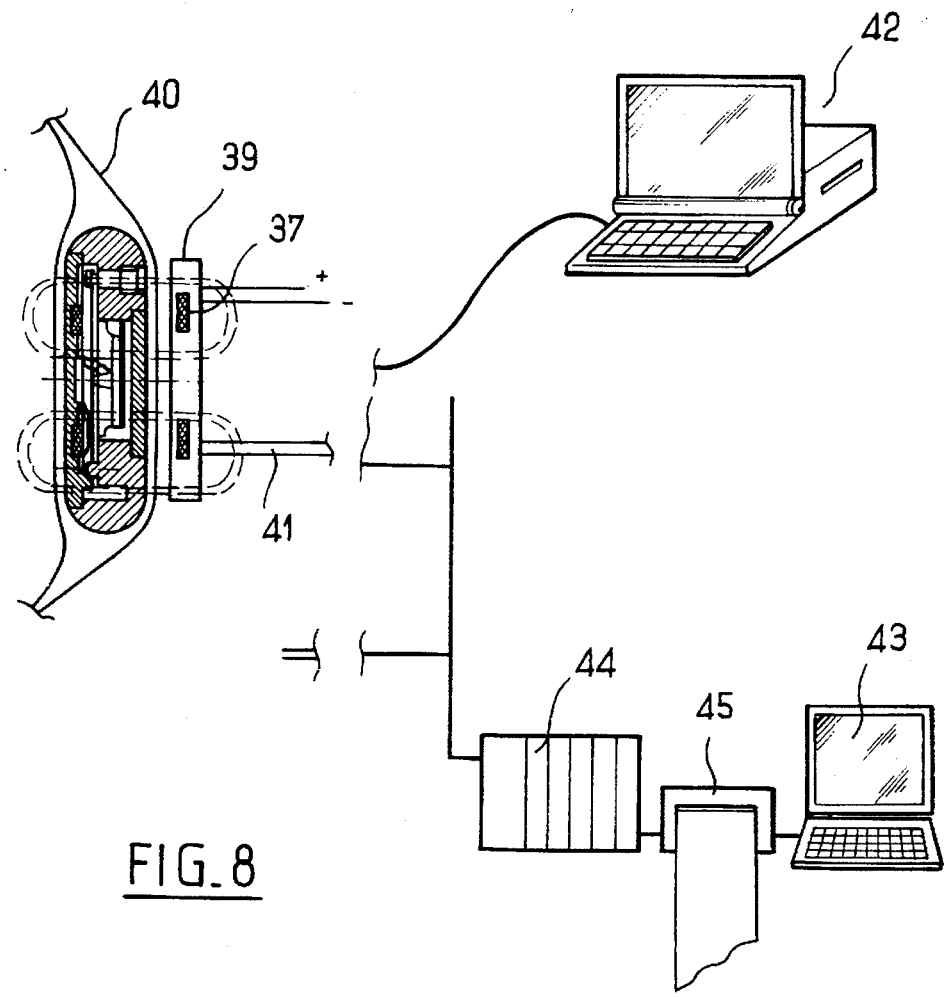
FIG_8

DEVICE FOR REGULATING THE FLOW OF CEREBROSPINAL FLUID IN A DRAINAGE CIRCUIT

The present invention relates to a device for regulating the flow of an organic liquid in an artificial drainage circuit extending between a production site and a resorption site in a patient. One of the main applications of the invention relates to draining cerebrospinal fluid in the event of hydrocephalus, for example, regardless of whether it is in the cranium or in the lumbar region.

Hydrocephalus is a disease that is caused, in particular, by the natural drainage paths for cerebrospinal fluid being blocked. This disease is treated by installing a bypass for passing the liquid either from the ventricles in the cranium or from the base of the spinal column to a resorption site, and in particular the peritoneum.

This bypass includes a pipe with a flow-regulating valve, and the entire assembly is placed beneath the skin of the patient.

Several types of valve are presently available on the market for performing this function. The simplest include valves of the non-return type. Such valves are constituted by a slitted tube whose slits widen when the pressure inside the tube overcomes the elastic force of the tube which tends to close the slits (to which must be added or subtracted the pressure that obtains in the portion of the pipe situated downstream from said valve). It may likewise have a valve member pressed against a seat by a calibrated spring defining a pressure threshold at which the valve opens.

One of the major drawbacks of such valves lies in their lack of adjustment means. Unfortunately, the characteristics of the valve need to be adapted to each patient as a function of the natural characteristics of the patient's organism, and for any given patient, the characteristics of the valve need to be modified over time as a function of the way the disease evolves. Replacing one valve with another having different characteristics, whether for the purposes of initial adjustment or during evolution of the disease, requires a surgical operation to be performed since the valve is implanted beneath the skin of the patient.

Adjustable valves have therefore been developed. These comprise a spring urging a valve member (a bead) against its seat and organized so that the rated value of the spring can be adjusted from the outside without performing surgery. A control member is coupled to the spring and is capable of rotating inside the housing of the valve. That member is responsive to a magnetic field and it can be magnetically coupled through the skin with a driving member for the purpose of changing its position. Such valves are generally complex, and thus of considerable size and volume, they are of debatable reliability, and they are liable to become wrongly adjusted on receiving a shock. In addition, they include metal elements that interfere with certain acts such as taking X-rays.

In general, given the small driving forces that can be implemented in valves of that type, they are very difficult to build. In addition, regularity of operation is very chancy, since equilibrium of the valve member once a flow is established through the valve is highly sensitive to variations in the pressure and in the viscosity of the liquid. In addition, the high degree of miniaturization of that type of valve gives rise to devices that are fragile and liable to be destroyed.

Furthermore, known valves operate in a manner that is subject to parameters that vary very considerably, particularly as a function of the position of the patient. Thus, in the standing position, the pressure difference between the production site and the resorption site may be as much as 400 mm of water column, whereas in the prone position, the pressure difference may be zero. Furthermore, the absolute pressure in particular in the ventricular cavities, varies depending on whether the patient is standing or prone (it increases in the prone position). In other words, seen from the valve, it appears that one of the sites is subject to large variations in pressure while the other site is subject to variations in pressure that are smaller but not negligible compared with the larger variations. Since known valves are adjusted to small opening pressures (of the order of 50 mm to 150 mm of water column), depending on the height of the water column in the circuit, the valve may remain closed when the patient is prone, may remain normally open while the patient is sitting, but may give rise to severe over-drainage when the patient is standing, which can give rise to cerebral collapse.

Document FR-A-2 655 535 discloses a valve whose operation is independent of the pressure difference that exists between the upstream and downstream sides of the valve member that regulates the drainage flow rate. Nevertheless, that valve is difficult to manufacture and to develop, requiring a great deal of accuracy in manufacture and a very fine choice material.

The present invention seeks to remedy the draw-backs of the valves presently in use since they do not provide a satisfactory solution to the problem of over-drainage, and of the valve disclosed in the above-mentioned document which has not been put on the market because of difficulties of manufacture and of development.

In addition, the design of the valve of the invention enables it to contain a sensor whereby it is possible to monitor a patient by acquiring a value for intracranial pressure either continuously or discretely, depending on the state of the patient, this making it possible to take action quickly before irreversible consequences have had time to appear due to the pressure in the cranium being too high or too low.

To this end, the present invention provides a device for regulating the flow of an organic liquid between a production site and a resorption site of a patient in a drainage circuit that extends between the two sites, one of the sites being a site of small pressure variation and the other being a site of large pressure variation, particularly as a function of the position of the subject, the device comprising a valve for implanting beneath the skin and connected by a first duct to one of the sites and by a second cut to the other site, the valve comprising a body defining an internal passage interconnecting the two ducts, a member for adjusting the section of said passage, and control means coupled to said adjustment member to displace it between a first position in which it closes the passage is closed and second positions in which the passage is opened to a controlled extent. According to the invention, the control means comprise a first chamber formed in the body and closed in sealed manner by a moving wall, a second chamber formed in the body and separated from the first by the moving wall, which second chamber forms a portion of the interconnecting passage and is connected to the duct coming from the site having small pressure variation, means for coupling the moving wall to the adjustment member, resilient means for returning the adjustment member towards its position in which it closes the interconnecting passage, and means for adjusting the magnitude of the return force.

Because of this basic disposition that provides the site having small variation in pressure with a large area (the area of the moving wall of the chamber) it is possible to develop a large force on the diaphragm, thereby modifying the force exerted by the resilient return member on the member for adjusting the through section. It is thus possible, using a single valve, having an acceptable operating point defined by construction and corresponding to one situation of the patient, to adjust the forces brought into play so that the valve takes up another operating point that is acceptable for another situation of the patient. The two selected situations are the prone and the standing positions of the patient, thereby ensuring that the valve also operates properly, i.e. under physiologically acceptable conditions, for intermediate situations.

In a preferred embodiment of the invention, the valve body possesses a third chamber into which the other portion of the internal passage connected to the other duct opens out, which chamber is separated from the second chamber by a wall provided with an opening surrounded by a valve seat, the adjustment member being a valve member that is movable relative to the seat.

The moving wall, which could be a piston sliding in a cylindrical opening formed in a portion of the valve body that delimits the first chamber, preferably includes a rigid central portion for coupling to the tail of the valve member and a flexible peripheral portion in the form of an annular diaphragm.

In a variant embodiment, the valve member is directly coupled to the rigid portion of the moving wall, the three chambers being superposed inside the body of the valve. Another variant embodiment is nevertheless to be preferred since it enables a valve to be manufactured that is thinner and in which the valve member is coupled to the rigid portion of the moving wall by means of a lever, the third chamber being disposed in the valve body at the same level as the first chamber.

It is highly advantageous to provide for the resilient member that returns the valve member against its seat to be a resilient flexible blade received in the first chamber, having one face merely pressing at both ends against abutments of the valve body (one of which is adjustable in position) while a middle portion of its other face merely presses against the center of the rigid portion of the moving wall.

In a preferred embodiment, the valve member is situated on same side of the seat at its side which is exposed to pressure from the site in which the organism liquid is resorbed. It thus performs a non-return function that prevents the production site from being contaminated from the resorption site. In addition, the first chamber should be filled with a liquid (to prevent gaseous diffusion through the walls of the valve) and should include a second deformable wall (or wall portion) subjected to the external subcutaneous pressure. Since, by construction, this chamber constitutes a reference, its sensitivity to subcutaneous pressure constitutes means for automatically compensating the operation of one of the components of the pressure acting on the other side of the diaphragm due to the subcutaneous pressure.

In addition, the structure of the valve of the invention presents the advantage of being adapted to making it simple to provide a device for measuring and monitoring, the pressure that obtains in the site having small pressure variation.

On its face facing the first chamber, the rigid portion of the moving wall possesses a projection against which the resilient blade presses and in which an electrical component is incorporated that has a characteristic that varies as a function of the pressure to which it is subjected, said component being coupled to a winding forming a passive oscillating circuit. In addition, the winding is situated in the first chamber with its axis substantially perpendicular to the surface of the skin of the patient once the valve has been implanted.

It is thus possible for the valve to co-operate with a pressure measuring pick-up, said valve acting as the passive element of a transponder, the pick-up being the active element and including, for this purpose, an oscillating circuit that comprises a winding and an electrical component identical to the component in the valve, but subject to no stress, and emitting a variable magnetic field of determined reference frequency and suitable for being placed close to the valve, and means for picking up the magnetic field emitted by the pressure-sensing oscillating circuit incorporated in the valve, for the purpose of comparing the reference frequency with the frequency of the responding magnetic field, from which the mechanical stress applied to the electrical component of the oscillating circuit of the valve can be deduced, which stress can be converted into a value for the pressure of the cerebrospinal fluid.

It will readily be understood that such a device is highly advantageous for acquiring data, for continuous surveillance of a patient in a critical stage of the illness, and in general for monitoring a patient when a valve is implanted so as to achieve the best possible adjustment of its operating parameters.

Other characteristics and advantages of the invention appear from the following description of various embodiments.

Reference is made to the accompanying drawings, in which:

FIG. 1 is a section view through a simplified valve for explaining how it operates.

FIG. 2 is a section view on a plane perpendicular to that of FIG. 1, likewise through a valve that is simplified for explanatory purposes, but that is representative of a preferred embodiment of the invention;

Figures 5, 6:
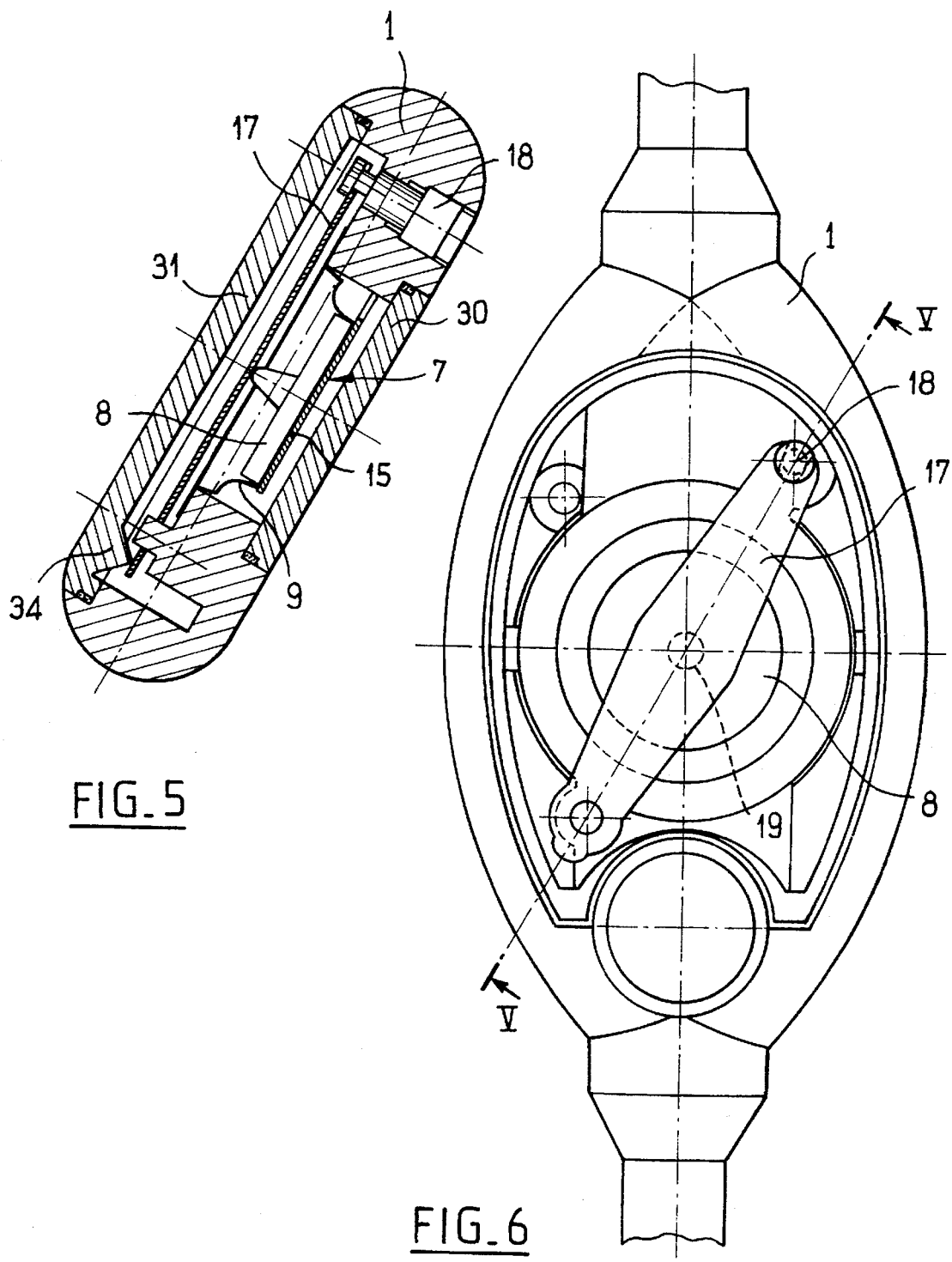

FIGS. 3, 4, 5, and 6 are views through a practical embodiment of a valve of the invention, FIGS. 3 and 5 being section views respectively on lines III—III and V—V of FIGS. 4 and 6 which are outside views of the valve of the invention;

FIG. 7 is a diagrammatic section view through a valve fitted with a passive transponder element; and FIG. 8 is a diagram of a system of the invention for measuring and monitoring intracranial pressure.

The valve of the invention shown in section in FIG. 1 comprises a body 1 connected via an orifice 2 to a duct 3 and via an orifice 4 to a duct 5. The orifice 2 opens out into a chamber 6 formed inside the body 1 and including a moving wall 7. This moving wall includes a rigid central portion 8 and an annular deformable flexible diaphragm connecting the central portion to the side wall of the chamber 6. Opposite the moving wall 7, the chamber 6 is delimited by a wall 10 provided with an orifice 11. The moving wall 7 also co-operates with the box 1 to delimit a chamber 12 which is filled with a liquid at atmospheric pressure. The wall of the box 1 delimiting the chamber 12 opposite to the diaphragm 7 includes a flexible portion 1a whereby the pressure outside the box is transmitted to the inside of the chamber 12.

The orifice 11 formed in the wall 10 provides communication between the chamber 6 and a third chamber 13 formed inside the valve body and leading to the duct 5. In the example of FIG. 1, the moving wall 7 directly carries a valve member 14 capable of closing the orifice 11 whose edge constitutes a seat for the valve member 14 and is fitted with any material that is suitable for providing a good seat for the valve member in a first position. The valve member 14 is secured to the rigid portion 8 of said moving wall and its position relative to the seat defines the through section between the chambers 6 and 13. The working section of this valve member is considerably smaller than the areas of the moving wall exposed to the pressure that obtains in the chambers 12 and 6, such that the influence of the pressure that obtains in the chamber 13 on the displacement of the moving wall is reduced.

In addition, the valve of the invention includes a resilient member for urging the valve member 14 against its seat. This resilient member is constituted by a resilient flexible blade 17 received in the chamber 12 that bears in simple (or hinged) manner via one of its ends 17a against the box and that bears in simple manner via its other end 17b against an adjustable abutment constituted by a screw 18 whose head is accessible from outside the box. In the middle of its other face, the blade 17 bears against a projection 19 carried by the rigid portion 8 of the moving wall 7 on its side opposite to that carrying the valve member. In a variant that is not shown, the projection may be replaced by a bead received in a small recess in the blade 17 and bearing against the rigid portion 8 of the diaphragm 9.

The structure operation, and adjustment of the valve are as follows.

The diaphragm 9 and the spring 17 are installed inside the box 1 and the chamber 12 is filled so that the following first test is satisfied: a fixed flow rate of liquid (e.g. 10 cm³/hour) is delivered to the valve via its orifice 2, and the spring 17 is adjusted so that the incoming liquid flows from the orifice 2 to the orifice 4 at atmospheric pressure. Thereafter, the orifice 4 is connected to a duct that establishes suction of about 300 mm or water column inside the chamber 13 and the pressure in the chamber 6 is measured. This pressure must be negative (suction) by a defined amount (e.g. lying in the range 0 mm to minus 100 mm of water column). Any valve which fails to satisfy this first criterion by construction is rejected.

Thereafter, adjustment is performed consisting in acting on the screw 18 so as to move the valve member towards its seat such that for a pressure in the chamber 13 of about minus 300 mm of water column, the pressure in the chamber 6 is practically zero (i.e. equal to atmospheric pressure) while the flow rate continues to be 10 cm3/hour. The valve is then ready to be implanted in a first application, i.e, on a drainage duct extending between a ventricular cavity of the brain (production site) and a peritoneal resorption site, for example. The implanted valve operates as follows. It is assumed that the valve is such that the value defined in the test of its construction is minus 50 mm of water column, and that it is used for the purpose of corresponding to the physiological data of a patient who, when prone, possesses an intraventricular pressure of 50 mm of water column, and substantially zero when standing, with a mean flow rate of cerebrospinal fluid being produced at 10 cm3/hour.

Thus, when the patient is standing, the pressure that obtains in the chamber 6 is zero, the pressure in the chamber 13 is minus 300 mm or water column, and the valve delivers 10 cm3/hour as during its adjustment. Fluctuations in intraventricular pressure lead to the position of the valve member 14 being servo-controlled to said fluctuating pressures. If the pressure drops, the spring 17 tends to urge the valve member towards its seat, the flow rate is reduced and the intraventricular pressure rises progressively until it becomes positive. Under such circumstances, the diaphragm tends to move the valve member away from the seat, so the flow rate increases and the pressure decreases.

With the patient subsequently taking up a prone position, the intraventricular pressure takes up a value of 50 mm of water column while the pressure in the chamber 13 is practically zero. Under such circumstances, because the diaphragm 9 moves the valve member 14 away from its seat, this pressure causes the through section to increase sufficiently for the flow rate through the orifice 11 to be kept constant even though the pressure difference between the chambers 6 and 13 is much smaller than it was when the patient was standing.

The valve of the invention is therefore adapted to proper draining without overdraining in the standing position and without blockage in the prone position. It may be observed in this application that, seen from the valve, the site having large pressure variation (300 mm of water column) is the resorption site, whereas the site having small pressure variation (50 mm of water column) is the production site.

The valve shown in FIG. 1 is, by construction, also suitable for a second "lumbar peritoneal" application. The idea is to drain the cerebrospinal fluid from the lumbar region of the spinal column (production site) to a zone of the peritoneum (resorption site).

In this case, the valve must satisfy, by construction, the following test (e.g. using the same values as before):

a fixed flow rate is delivered at atmospheric pressure to the valve via the orifice 4 and the spring is placed so that the liquid leaves via the orifice 2 without increasing the inlet pressure 4;

thereafter the orifice 4 has a duct connected thereto for establishing a pressure rise of 400 mm to 500 mm of water column at the inlet and the pressure in the chamber 6 should be seen to become slightly negative (about 50 mm to 100 mm of water column) still for the same flow rate.

Thereafter, the screw 18 is adjusted so that the pressure in the chamber 6 is practically zero.

A lumbar peritoneal valve constructed in this way section at the valve seat quickly. It should also be observed that in this embodiment the valve member 14 is mounted so as to act as a non-return valve. It will be understood that unlike the configuration of FIG. 1 and for an application in which the resorption site is connected to the orifice 4, it opens in the flow direction. Any reverse flow will then tend to press it against its seat. The sensitivity of this effect can be increased by the connection between the lever 15 and the valve member 14 being provided with play along the valve member.

In FIG. 2, the resilient member for urging the valve member 14 against its seat is represented in the form of a traction spring 21 that is housed in the chamber 6 and that can therefore be adjusted by displacing its coupling point 22 remote from the coupling between the spring and the valve member 14. The means for adjusting the position of this coupling element 22 are not shown in this figure.

In this figure, it can also be seen that there is a portion of the deformable wall 1a that makes it possible to cause the pressure that obtains inside the chamber 12 to be equal to the subcutaneous pressure of the patient. The advantage of this disposition is that it makes it possible to eliminate variations in the pressure acting against the diaphragm in the chamber 6 that are due solely to variations in subcutaneous pressure.

FIGS. 3 to 6 show a valve of the invention in a more practical configuration. These figures show most of the elements as described above with the same references. In this case, the body 1 is in the form of an elongate ovoid of a biologically compatible synthetic material and possessing a middle wall 23 provided with a central orifice closed by the moving wall 7, said wall 23 separating the chamber 6 from the chamber 12. The two chambers 6 and 12 are delimited with the body 1 by covers likewise made of biologically compatible material and given respective operates as follows. With the patient standing, the valve passes liquid as tested with an inlet pressure of 400 mm to 500 mm of water column. In the prone position, the pressure in the chamber 6 will rise, moving the valve member 14 away from its seat, thereby increasing the through section for the fluid which is at substantially zero inlet pressure but which does not have any head losses to overcome in order to flow away naturally.

In a lumbar peritoneal application, and as seen from the valve, it is the resorption site that has small pressure variation while it is the fluid producing site that has large pressure variations.

FIG. 2 shows some of the elements described above with the same references. In this embodiment, it will be seen that the diaphragm 9 is fine and has no elastic stiffness. The diaphragm is fixed by any appropriate means (adhesive, ultrasound welding, . . . ) both to the walls of the chamber and to the central portion. The surfaces of all of the walls of the chambers 6, 12, and 13, and also of the orifices 2 and 4 are covered in carbon by means of a known treatment whereby an acetylene atmosphere is cracked under a vacuum. In this case, the valve member 14 is coupled to a lever 15 secured to the rigid central portion 8 of the moving wall 7, said lever 15 bearing simply or by means of a hinge against the box 1 at its end 16 that is opposite from its end carrying the valve member 14. The presence of this lever has two advantages. Firstly it makes it possible to place the chamber 13 at the same level as the chamber 12, thereby making it possible to reduce the height of the valve of the invention in comparison with an embodiment as shown in FIG. 1, and as can be seen more precisely in the following figures. In addition, this lever provides amplification of the displacement of the moving wall 7 as seen by the valve member 14, thereby making it possible to achieve a large change in through references 30 and 31, the inside faces of the covers being likewise treated so as to be covered in carbon. The covers are applied to the body by any appropriate means. The lever 15 has its end 16 pivoting on a boss 32 of the cover 30 while its opposite end is given the shape of a fork 33 that co-operates with the tail of the valve member 14 so as to urge it against its seat under drive from the spring blade 17 as transmitted by the projection 19 and the rigid portion 8 of the moving wall of the lever 15. The sensitivity of the valve can be improved by allowing play along the tail of the valve member in the connection between the lever 15 and the valve member 14. In the event of a pressure reversal causing fluid to return from the resorption site towards the production site, the lever moves away from the seat and the valve closes under the effect of a reverse flow beginning. FIG. 4 is a drawing showing the valve as seen looking along F in FIG. 3, with the cover 30 removed.

FIG. 6 is a view along G of FIG. 3, with the cover 31 removed. It can be seen that the flexible spring blade 17 is disposed diagonally across the lever 15, said blade 17 co-operating with the screw 18 and with a boss 34 of the cover 31. When the screw 18 is loosened, the blade 17 is forced against the projection 19 secured to the rigid portion 8 of the moving wall 7. Conversely, when the screw 18 is moved inwards, the spring 17 is relaxed. FIG. 5 is a section through the valve on line V—V of FIG. 6, i.e. a line running along the longitudinal direction of the spring blade 17.

Finally, in FIGS. 3 and 4, the shape given to the wall portion 1a can be seen, i.e. a hollow plug having fine walls 1b that close an orifice in the cover 30.

FIG. 7 is a section view identical to FIG. 5 but through a variant embodiment of the invention that enables the flow rate regulating valve to act also as an instrument for measuring and monitoring the pressure of the cerebrospinal fluid inside the cranium. In addition to the elements that have already been described and that are given the same references in FIG. 7, this valve further includes, for the purpose of providing a sensor that detects the intracranial pressure, an oscillating electrical circuit comprising: a winding 35; a component 36 that is constituted in this case by a quartz crystal and that is interposed between the rigid portion 8 of the moving wall and the projection 19 bearing against the spring blade 17, and having a resonant frequency that varies as a function of the compression stress to which it is subjected; and a reference crystal 36a that is not stressed. Alternatively, the component 36 could be constituted by a strain gauge placed on one of the faces of the spring blade 17. The circuit would then constitute a relaxation oscillator. It will be understood that the characteristic which varies as a function of the pressure that obtains in the chamber 12 of the component 36 (crystal or strain gauge) changes the resonant frequency of the oscillating circuit.

The oscillating circuit integrated in the valve of the invention constitutes the passive element of a transponder whose active element is constituted by an exciter oscillating circuit having a coil 37. FIG. 8 illustrates this active element assembled in an electrode 39 that can be placed in the vicinity of the valve of the invention when it is implanted beneath the skin 40 of a patient. Excitation of the oscillating circuit 37 generates a magnetic field of determined frequency that will induce current in the passive oscillating circuit of the valve at a frequency that is a function of the difference between the strain states of the components 36 and 36a. The induced current modulated in this way-responds by creating a magnetic field that can be picked up by the electrode 39, which field has a beat type frequency that is representative of the strain state of the crystal 36. To ensure maximum magnetic coupling between the active and passive oscillating circuits, the coils must be parallel, so the coil 35 must have its axis perpendicular to the skin of the patient when the valve is implanted.

Naturally the active and passive oscillating circuits include electronic components that are not described but are known per se such as capacitors and transistors.

The output 41 of the electrode 39 delivers the beats that result from the frequency difference between the transmitted signal and the response signal, which frequency difference can be transmitted to and processed by a microprocessor 42, whereby the changes in the measured pressure can be monitored and followed.

FIG. 8 shows that a microprocessor 43 associated with memories 44 and a printer 45 can be suitable for monitoring a plurality of patients each fitted with a sensor of the invention. It is also possible to connect the output 41 of the transponder to a portable recording apparatus enabling proper operation of the implanted valve to be verified and monitored.

The above-described closure member may be constituted by any suitable valve member. In particular, it may be constituted by a bead that is urged by two springs in opposition, the spring blade 17 acting on the rigid portion of the moving wall and by the lever 15 acting on the bead in a direction that tends to unload the spring whose effect is to open the valve member.

The invention is also applicable to artificial drainage of other organic fluids, such as ascites (serosities in the peritoneum).

We claim:

1. A device for regulating the flow of an organic liquid between a production site and a resorption site of a patient in a drainage circuit that extends between the two sites, one of the sites being a site of small pressure variation and the other being a site of large pressure variation as a function of the position of the patient, the device comprising a valve for implanting beneath the skin and for connecting by a first duct to one of the sites and by a second duct to the other site, the valve comprising a body defining an internal passage interconnecting the two ducts, a member for adjusting the section of said passage, and control means coupled to said adjustment member for moving said adjustment member between a first position in which the passage is closed and second positions in which the passage is opened to a controlled extent, wherein the control means comprise a first chamber formed in the body and closed in sealed manner by a diaphragm, a second chamber formed in the body and separated from said first chamber by the diaphragm, which second chamber forms a portion of the internal passage and is connected to the duct coming from the site having small pressure variation, means for coupling the diaphragm to the adjustment member, resilient means separate from said diaphragm for returning the adjustment member towards said first position and means for adjusting said resilient means.

2. A device according to claim 1, wherein the valve body includes a third chamber forming an other portion of the internal passage connected to the duct coming from the site having large pressure variation, which chamber is separated from the second chamber by a wall provided with an opening surrounded by a valve seat, the adjustment member being a valve member that is movable relative to the seat.

3. A device according to claim 2, wherein the diaphragm includes a rigid central portion for coupling to a stem of the valve member and a flexible peripheral portion.

4. A device according to claim 3, wherein the valve member is directly coupled to the rigid portion of the diaphragm, the three chambers being superposed inside the body of the valve.

5. A device according to claim 3, wherein the valve member is coupled to the rigid portion of the diaphragm by means of a lever, the third chamber being disposed in the valve body at the level of the first chamber.

6. A device according to claim 3, wherein the resilient return member is housed in the first chamber and cooperates with the rigid portion of the diaphragm.

7. A device according to claim 2, wherein the valve member is situated on the side of the valve seat which is exposed to pressure from the organic liquid resorption site.

8. A device according to claim 1, wherein the first chamber is filled with liquid and includes a deformable wall subjected to the outside pressure.

9. A device according to claim 6, wherein the resilient member for returning the valve member against the valve seat is a resilient flexible blade having one face bearing in simple manner at both ends against abutments of the valve body, with the middle portion of another face of the flexible blade bearing in simple manner against the center of the rigid portion of the diaphragm, one of the two abutments of the valve body being adjustable in position perpendicularly to the faces of the blade.

10. A device according to claim 9, wherein the adjustable abutment is formed by the end of a screw cooperating with a tapped orifice in the body and projecting into the first chamber, the head of the screw being accessible and drivable from outside the body of the valve.

11. A device according to claim 9, wherein the rigid portion of the diaphragm includes, on a face facing towards the first chamber, a projection against which said resilient blade bears, the device further including an electrical sensing component of the contact force between said blade and said projection, said sensing component being connected to a winding forming a passive oscillating circuit.

12. A device according to claim 11, wherein the winding is situated in the first chamber, and an axis being substantially perpendicular to the surface of the skin of the patient when the valve is implanted.

13. A device according to claim 11, wherein the electrical sensing component is a quartz crystal interposed between the rigid portion of the diaphragm and the projection.

14. A device according to claim 11, wherein the electrical sensing component is a strain gauge placed on the spring blade.

15. A device for measuring the pressure in the site having small pressure variation of a patient fitted with a regulator device according to claim 11, including an oscillating circuit comprising a winding and an electrical component identical to the component included in the valve, and subjected to no stress, for emitting a variable magnetic field of determined reference frequency and for being placed in the vicinity of the valve and including means for picking up the magnetic field emitted by the oscillating circuit incorporated in the valve, for comparing said reference frequency to the frequency of the magnetic field emitted by said oscillating circuit, for deducing therefrom the mechanical stress to which said electrical component of the oscillating circuit in the valve is subjected, and for converting said stress into a value for the pressure of cerebrospinal fluid.

16. A device according to claim 1, wherein the inside surfaces of the body adjacent to the internal passage are covered in carbon.

* * * * *